United States Patent [19]

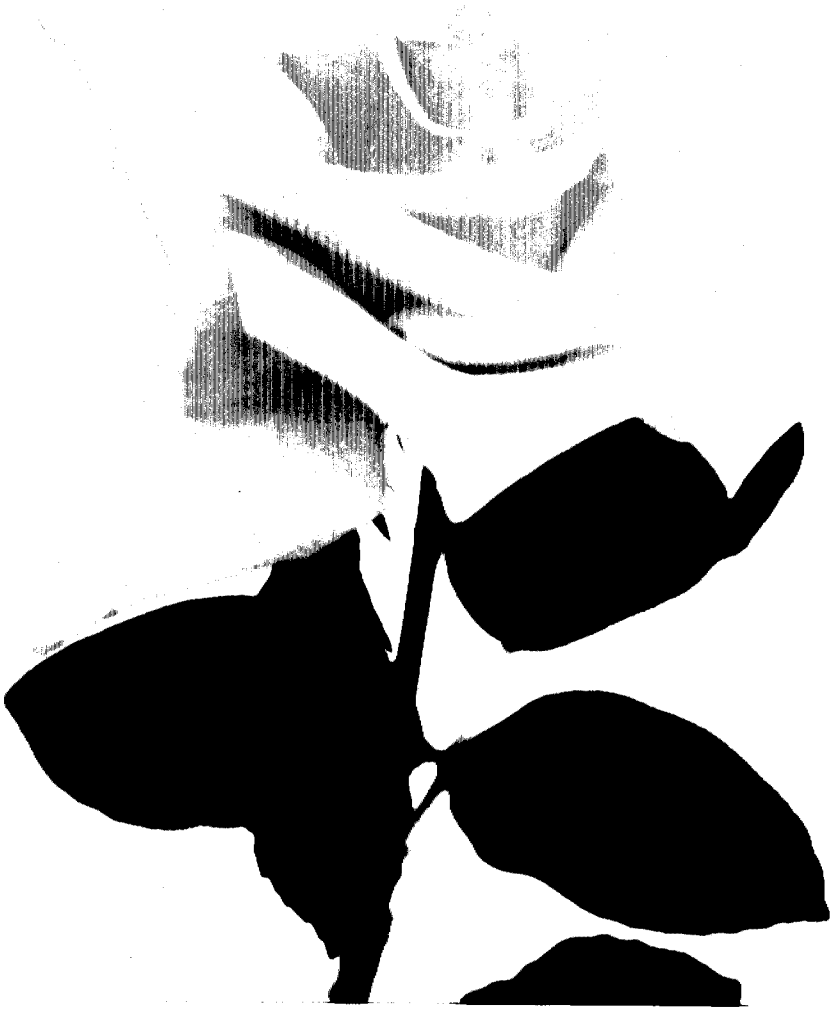

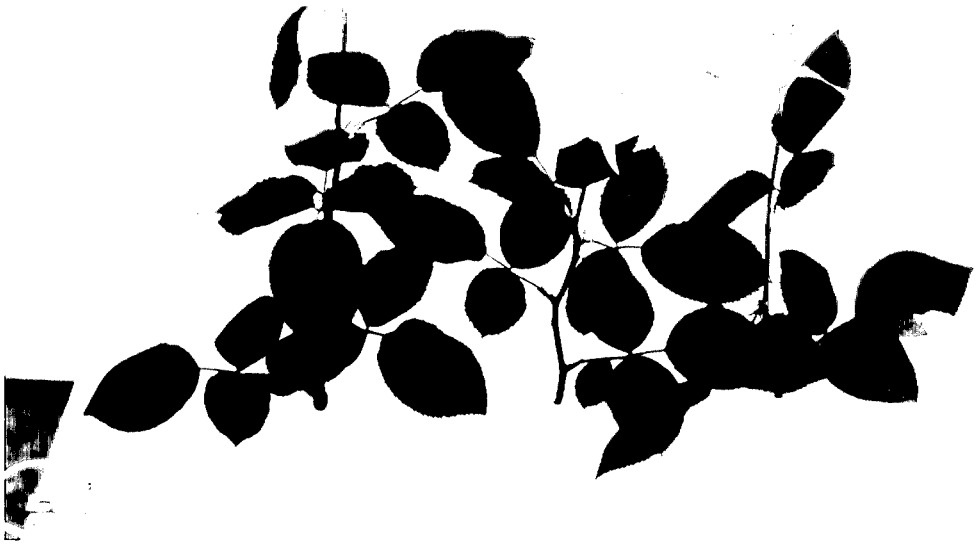
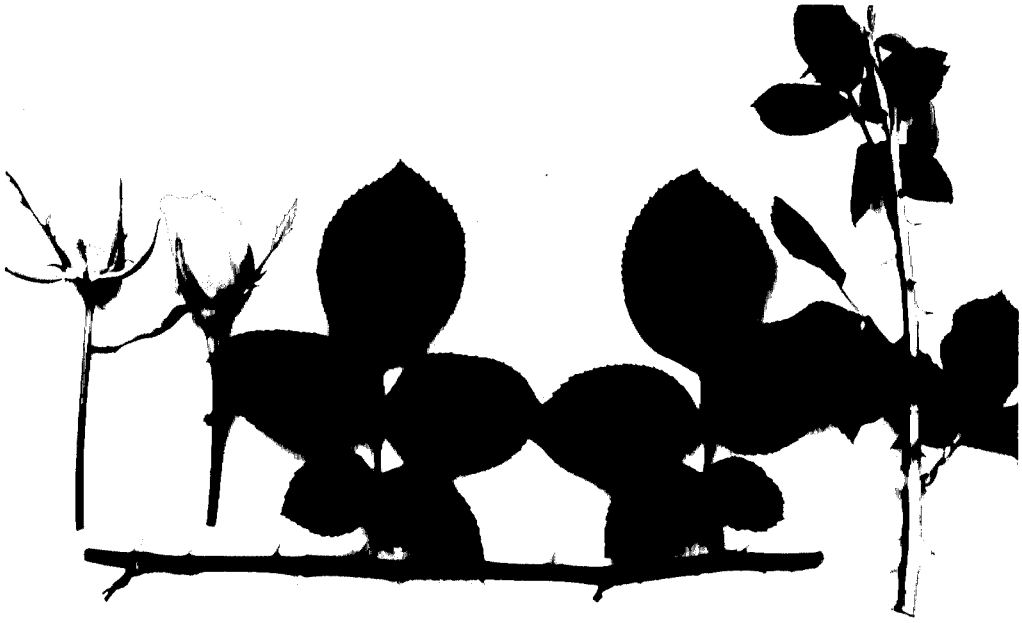

Shirakawa

[11] Patent Number: Plant 5,633

[45] Date of Patent: Jan. 14, 1986

[54] TEA ROSE NAMED TOBONE

[75] Inventor: Takeshi Shirakawa, Gamagori, Japan

[73] Assignee: Toshio Nakashima, San Leandro, Calif.

[21] Appl. No.: 596,000

[22] Filed: Mar. 26, 1984

[51] Int. Cl.[4] ..... A01H 5/00

[52] U.S. Cl. ..... Plt./19

[58] Field of Search ..... Plt./19

*Primary Examiner*—Robert E. Bagwill

*Attorney, Agent, or Firm*—Chas. W. Rummler

[57] ABSTRACT

A new variety of hybrid tea rose intended mainly for greenhouse culture and the commercial production of cut flowers, characterized by a continuous and profuse production of very large red-purple blooms carried on very long, strong stems; its urn-shaped buds which open slowly to produce well formed flowers having large petals which tend to marginally turn under and form points; its free branching and vigorous growth habit; its abundant production of glossy foliage and long last vase life; and its resistance to diseases.

3 Drawing Figures

BACKGROUND OF THE NEW PLANT

My new variety of rose plant is the result of breeding efforts carried on by me at 20 Koyama, Takenoya-cho, Gamagori-shi, Aichi Ken, Japan, with the object of producing a red-purple rose having an upright growth habit with very long stems and an excellent vase life with resistance to mildew, rust, and black spot. This plant originated as a seedling derived by my crossing of an unnamed seedling with the variety "Prominent" (U.S. Plant Pat. No. 3,380), the unnamed seed parent having resulted from the cross of an unnamed seedling by "Happiness" (U.S. Plant Pat. No. 911), in my greenhouse breeding facilities in Japan. The form and beauty of the flowers of this new plant and its very fine growth habit led me to propagate this plant through several generations, by budding, which showed that the novel characteristics of this plant would hold true from generation to generation and as a result, commercial propagation of this plant, by budding, is now being carried on under my direction in Japan.

DESCRIPTION OF THE DRAWINGS

My new variety of rose plant is illustrated by the accompanying photographic drawings, sheet one of which shows a fully opened flower together with some foliage; sheet two which includes an upper photographic drawing showing several stages of bud opening, and a lower drawing showing the upper and underside views of typical leaves together with specimens of young and old wood, and a bud in the first of its opening stages. The flower colors shown in the drawings are as nearly true as can be obtained by careful conventional photographic procedures.

DESCRIPTION OF THE NEW PLANT

The following is a detailed description of my new rose plant with color designations according to The R.H.S. Colour Chart published by The Royal Horticultural Society of London, England.

THE PLANT

Origin: Seedling.

Parentage:

*Seed parent.*—An unnamed seedling derived from the crossing of another unnamed seedling with "Happiness" (U.S. Plant Pat. No. 911).

*Pollen parent.*—"Prominent" (U.S. Plant Pat. No. 3,380).

Classification:

*Botanic.*—Hybrid Tea.

*Commercial.*—Greenhouse rose.

Form: Compact bush.

Habit: Upright and much branched.

Growth: Vigorous.

Height: About 170 to 180 centimeters at 2 years.

Canes: Very strong, sturdy and upright.

Foliage:

*Quantity.*—Abundant.

*Number of leaves.*—9 to 11 on flower stem from hook spaced about 3.5 to 3.8 centimeters apart.

Shape of leaf.—Oblong with serrated margins and acute apex.

*Leaflets.*—Shape: Ovate with acute apex and serrated margins. Size: About 5.8 to 8.2 centimeters long and about 3.5 to 7.8 centimeters wide. Number: 3 to 5. Texture: Leathery. Aspect: Glossy. Color: Upper side — Green 137C (greenhouse); Green 139A (outside). Under side — Green 134D (greenhouse): Green 138B (outside). Petioles: 1.9 to 2.1 centimeters long. Petiolule: 2.9 to 3.2 centimeters long including stipules; 1.9 to 2.1 centimeters along without stipules. Ribs and Veins: Prominent; slightly depressed on upper side and more prominent on underside. Thorns: Size: About 0.6 to 1.2 centimeters long. Most are hooked slightly downward. Color: Greyed-Orange 166B.

THE BUD

Form: Pointed.

Size: About 4.2 to 5 centimeters long and about 1.8 centimeters in diameter.

Color:

*When sepals first divide.*—Red-Purple 58B.

*When petals begin to unfurl.*—Red-Purple 57D.

Sepals: The sepals stand up initially and as the flower opens the sepals curl back and fold down along the stem.

*Shape.*—Ovate-acuminate; some sepals have the appearance of leaves.

*Color.*—Inside — Yellow-Green 148D; Outside — Green 143C.

Calyx:

Shape.—Pear-shaped.

*Size.*—Small.

*Aspect.*—Smooth.

Peduncle:

*Length.*—About 3.0 to 3.4 centimeters.

*Strength.*—Erect, sturdy, upright.

*Color.*—Greyed-red 178A.

THE FLOWER

Blooming habit: Continuous and abundant.

Borne: Singly on strong stems.

Size: Very large; about 12 to 13 centimeters in diameter and about 6 centimeters deep.

Shape:

*When bloom first opens.*—Flat with high center. As bloom matures the petals reflex to open center.

Petalage:

*Number of petals.*—25 to 29.

*Arrangement.*—Imbricated.

*Form.*—Outside and intermediate petals are obvate with entire margins which tend to turn under and form points at petal apex.

*Texture.*—Leathery.

*Appearance.*—Satiny.

*Color.*—Outer petals: Top side — Red-Purple 58C. At base — Yellow-Orange 21B. Reverse side: Margin: — Red-Purple 57D. Center — Red-Purple 57D. Base — Yellow-Orange 20B. Inside petals: Face side: Body — Red-Purple 58B. Base — Orange 25A. Reverse side: Body — Red-Purple 58B. Base — Orange 25A.

Peduncle.—Length: About 9 to 10 centimeters. Character: Sturdy and upright. Color: Green 141C.

*Persistence.*—Petals stay on stem under greenhouse conditions; when grown outside petals eventually drop leaving a moderately clean bush.

*Fragrance.*—Slight.

*Lasting quality.*—On plant — more than 15 days. As cut flower — 10 to 15 days.

REPRODUCTIVE ORGANS

Stamens:

*Anthers.*—Number: 75 to 100. Length: About 0.2 centimeters. Arrangement: Slightly introrse. Color — Yellow-Orange 16A.

*Filaments.*—Length: About 1.2 centimers. Color: Orange 25A.

*Pollen.*—Color — Yellow-Orange 16A.

Pistils:

*Styles.*—Number: 65 to 75. Length: About 1.1 centimeters.

*Stigmas.*—Color — Yellow 12C.

*Ovaries.*—Covered with silvery white hairs with calyx tube in ovid or egg shape.

Most resembles "Prominent" (U.S. Plant Pat. No. 3,380) in form but with a distinctive fuschia or red-purple color more like "Better Times" (U.S. Plant Pat. No. 23), and with excellent vase life, very strong stems, and moderate disease resistance.

I claim:

1. A new and distinct rose plant, substantially as herein shown and described, characterized by the brilliant red-purple color of its very large flowers which are borne on long, strong stems, its year-around abundant production of long-lasting blooms, and its disease resistance.

* * * * *